US006922591B2

(12) United States Patent
Single

(10) Patent No.: US 6,922,591 B2
(45) Date of Patent: Jul. 26, 2005

(54) MULTIPLE BATTERY MANAGEMENT SYSTEM

(75) Inventor: Peter Single, Lane Cove (AU)

(73) Assignee: Cochlear Limited, Lane Cove (AU)

( * ) Notice: Subject to any disclaimer, the term of this patent is extended or adjusted under 35 U.S.C. 154(b) by 294 days.

(21) Appl. No.: 09/962,898

(22) Filed: Sep. 25, 2001

(65) Prior Publication Data

US 2002/0076071 A1 Jun. 20, 2002

(30) Foreign Application Priority Data

Sep. 26, 2000 (AU) ............................................ PR0366

(51) Int. Cl.[7] ............................................ A61N 1/36
(52) U.S. Cl. ............................................ 607/57
(58) Field of Search ...................... 607/1, 2, 34, 55–57

(56) References Cited

U.S. PATENT DOCUMENTS

| | | | | |
|---|---|---|---|---|
| 4,532,930 A | | 8/1985 | Crosby et al. | |
| 5,411,537 A | | 5/1995 | Munshi et al. | |
| 5,702,431 A | | 12/1997 | Wang et al. | |
| 5,739,596 A | * | 4/1998 | Takizawa et al. | 307/66 |
| 6,067,474 A | | 5/2000 | Schulman et al. | |
| 6,223,077 B1 | * | 4/2001 | Schweizer et al. | 607/5 |
| 6,586,850 B1 | * | 7/2003 | Powers | 307/85 |

FOREIGN PATENT DOCUMENTS

| | | |
|---|---|---|
| GB | 2 279 827 | 6/1993 |

* cited by examiner

*Primary Examiner*—George R. Evanisko
(74) *Attorney, Agent, or Firm*—Jagtiani + Guttag

(57) ABSTRACT

A power management system for a power supply (43) providing power to electrical equipment, such as a totally implantable prosthetic hearing implant (40). The power supply (43) can comprise a first rechargeable battery and at least one further rechargeable battery that each independently provide power to the implant (40) through a switching means. The management system comprises a management means for controlling the operation of the switching means to place the system in a first state where the implant (40) can draw power from only the first battery or at least in a further state where the implant (40) can draw power from only said at least one further battery.

20 Claims, 3 Drawing Sheets

MULTIPLE BATTERY MANAGEMENT SYSTEM

CROSS-REFERENCE TO RELATED APPLICATIONS

This application claims the priority of AU Provisional App. No. PR0366, filed on Sep. 25, 2001. The entire disclosure and contents of the above patents and applications are hereby incorporated by reference.

FIELD OF THE INVENTION

The present invention relates to a power supply for an implant, such as a prosthetic hearing implant, and in particular, to a power supply having a plurality of rechargeable batteries and a management system for controlling the use of the batteries by the implant.

BACKGROUND ART

Hearing loss, which may be due to many different causes, is generally of two types, conductive and sensorineural. Of these types, conductive hearing loss occurs where the normal mechanical pathways for sound to reach the hair cells in the cochlea are impeded, for example, by damage to the ossicles. Conductive hearing loss may often be helped by use of conventional hearing aid systems, which amplify sound so that acoustic information does reach the cochlea and the hair cells.

In many people who are profoundly deaf, however, the reason for deafness is sensorineural hearing loss. This type of hearing loss is due to the absence of, or destruction of, the hair cells in the cochlea which transduce acoustic signals into nerve impulses. These people are thus unable to derive suitable benefit from conventional hearing aid systems, because there is damage to or absence of the mechanism for nerve impulses to be generated from sound in the normal manner.

It is for this purpose that prosthetic hearing implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4,532,930, the contents of which are incorporated herein by reference, provides a description of one type of traditional prosthetic hearing implant system.

Prosthetic hearing implant systems have typically consisted of two key components, namely an external component commonly referred to as a processor unit, and an implanted internal component commonly referred to as a stimulator/receiver unit. Traditionally, both of these components have cooperated together to provide the sound sensation to an implantee.

The external component has traditionally consisted of a microphone for detecting sounds, such as speech and environmental sounds, a speech processor that converts the detected sounds and particularly speech into a coded signal, a power source such as a battery, and an external antenna transmitter coil.

The coded signal output by the speech processor is transmitted transcutaneously to the implanted stimulator/receiver unit situated within a recess of the temporal bone of the implantee. This transcutaneous transmission occurs through use of an inductive coupling provided between the external antenna transmitter coil which is positioned to communicate with an implanted antenna receiver coil provided with the stimulator/receiver unit. This communication serves two essential purposes, firstly to transcutaneously transmit the coded sound signal and secondly to provide power to the implanted stimulator/receiver unit. Conventionally, this link has been in the form of a radio frequency (RF) link, but other such links have been proposed and implemented with varying degrees of success.

The implanted stimulator/receiver unit typically includes the antenna receiver coil that receives the coded signal and power from the external processor component, and a stimulator that processes the coded signal and outputs a stimulation signal to an intracochlea electrode assembly which applies the electrical stimulation directly to the auditory nerve producing a hearing sensation corresponding to the original detected sound.

The external componentry of the prosthetic hearing implant has been traditionally carried on the body of the implantee, such as in a pocket of the implantee's clothing, a belt pouch or in a harness, while the microphone has been mounted on a clip mounted behind the ear or on a clothing lapel of the implantee.

More recently, due in the main to improvements in technology, the physical dimensions of the speech processor have been able to be reduced allowing for the external componentry to be housed in a small unit capable of being worn behind the ear of the implantee. This unit has allowed the microphone, power unit and the speech processor to be housed in a single unit capable of being discretely worn behind the ear, with the external transmitter coil still positioned on the side of the implantee's head to allow for the transmission of the coded sound signal from the speech processor and power to the implanted stimulator unit.

This need for a transmitter coil further requires leads and additional componentry which add to the complexity of such systems as well as being quite noticeable. Nevertheless, the introduction of a combined unit capable of being worn behind the ear has greatly improved the visual and aesthetic aspects for prosthetic hearing implant implantees and provided a degree of freedom of movement for implantees that had previously not been possible with body worn devices.

While traditional prosthetic hearing implants have proven very successful in restoring hearing sensation to many people, the construction of the conventional implant with its external electronic components has limited the circumstances in which the implant can be used by a implantee, For example, implantees cannot wear the devices while showering or engaging in water-related activities. Most implantees also do not use the devices whilst asleep due to discomfort and the likelihood that the alignment between the external transmitter coil and the internal receiver coil will be lost due to movements during sleep. Therefore, with the increasing desire of prosthetic hearing implant implantees to lead a life that is the equivalent of a naturally hearing person, there exists a need to provide a system which allows for total freedom with improved simplicity and reliability.

Because of this need, fully implantable systems that do not require external componentry for operation have been postulated. One type of system which has been proposed is described in U.S. Pat. No. 6,067,474 by Advanced Bionics Corporation and Alfred E Mann Foundation for Scientific Research. This system attempts to provide all system components implanted in the implantee, and includes a microphone placed in the ear canal which communicates with a conventionally positioned stimulator unit via a conventional RF link. There is further described a battery unit which can be integral with the stimulator unit or separate therefrom.

Such a system provides further complications as it requires surgical implantation of a number of components and hence complicates the surgical procedure The system also maintains the need for an RF link during normal operation between implanted components which increases overall power requirements of the system and unnecessary drains the internal battery supply. Also, such a system requires multiple implanted casings and the necessity for communications between internal components thereby increasing the likelihood of system failure due to component malfunction. In the event of a system malfunction, the procedure required to correct such a device failure becomes further complicated due to the number of implanted components and the complex communication channels between all components.

The present applicant has also proposed a totally implanted prosthetic hearing implant system in International Application No. PCT/AU01/00769. This system has the advantage that all of the components are provided in a single unit that is able to be implanted by conventional surgical procedures.

A problem with totally implanted system is that the systems are reliant on power sourced from rechargeable power sources implanted with the implant. A well understood problem with rechargeable batteries is that-the batteries can only undergo a particular maximum number of recharging cycles before the performance of the battery degrades to a level where the battery is essentially unusable A further problem with rechargeable batteries is that if they are discharged before being fully charged, or conversely, are charged before being fully discharged, their overall capacity may be reduced. When such batteries are implanted, all means should be undertaken to maximize the batters operating life as the replacement of such batteries requires a surgical procedure.

These problems are further compounded by the fact that in prosthetic hearing implant applications, the recharging process for the implanted power source is heavily reliant on the implantee's ability to dedicate a particular amount of their time to recharge the internal power source when necessary. This requires the implantee to closely monitor the charge status of their system and ensure that the power source is recharged only when the battery has been fully discharged. Therefore, such an onus can impinge greatly on the implantee's lifestyle, thereby reducing the implantee's freedom to use such a totally implanted device, which is one of the great benefits of providing a totally implanted device in the first instance.

It is therefore an object of the present invention to provide a system designed to maximize the performance of batteries installed in totally implanted prosthetic hearing implants and other implants that may rely on battery power.

It is a further object of the present invention to provide an internal power management system that ensures that the charging/recharging cycles of the implanted device occur with minimal interruption to the implantee's regular lifestyle and with minimal input from the implantee.

SUMMARY OF THE INVENTION

According to a first aspect, the present invention is a power management system for a power supply providing power to electrical equipment, the power supply comprising a first rechargeable battery and at least one further rechargeable battery, with each battery independently providing power to the electrical equipment through a switching means, wherein the management system comprises a management means for controlling the operation of the switching means to place the system in a first state where the electrical equipment draws power from only the first battery or at least in a further state where the electrical equipment draws power from only said at least one further battery.

In one embodiment of this aspect, the switching means is operable by the management means to place the system ill another state where the electrical equipment does not or cannot draw power from the first battery or said at least one further battery of the power supply. The management means will typically operate the switching means to place the power supply in said another state when another power source is available for the electrical equipment. An example of another power source may comprise an external power source.

In one embodiment, the switching means is adapted to ensure that when the first battery is in electrical communication with the electrical equipment, said at least one further battery is not in electrical communication with that equipment receiving power from the first battery, and vice versa. The switching means can comprise a switch that switches an electrical conductor extending to the electrical equipment from being in electrical communication with an output of the first battery to an output of said at least one further battery, and vice versa. When the system is in said another state, the switch can ensure the electrical conductor is not in electrical communication with the outputs of the batteries.

In a further embodiment, the management means only allows power to be drawn from a battery after that battery has been fully charged or reached a pre-determined maximum level of charge. It is also preferred, that the management means only allows a battery to be charged after that battery has reached a predetermined minimum level of charge. For example, the management means may only allow a battery to be recharged once it has been fully discharged.

In a further embodiment, when the power supply is in the first state, said at least one further battery can be recharged. It will be appreciated that recharging of said at least one further battery will be only be possible if a battery charger is available for connection to said at least one further battery. Conversely, when the power supply is in the further state, the first battery can be recharged. Again, recharging of the first battery will only be possible if the battery charger is available for connection to the first battery.

One example of the electrical equipment is a tissue-stimulating prosthesis adapted for implant in an implantee's body, such as a prosthetic hearing implant.

According to a second aspect, the present invention is a power management system for a power supply providing power to a prosthetic hearing implant, the power supply comprising a first rechargeable battery and at least one further rechargeable battery, with each battery independently providing power to the prosthetic hearing implant through a switching means, wherein the management system comprises a management means for controlling the operation of the switching means to place the system in a first state where the prosthetic hearing implant draws power from only the first battery or at least in a further state where the prosthetic hearing implant draws power from only said at least one further battery.

According to a third aspect, the present invention is a power management system for a power supply providing power to electrical equipment, the power supply comprising a first rechargeable battery and at least one further rechargeable battery, with each battery independently providing power to the electrical equipment through a switching means, the management system comprising a management means for controlling the operation of the switching means to place the system in a first state where the electrical equipment draws power from only the first battery or at least in a further state where the electrical equipment draws power from only said at least one further battery, and wherein when the system is in said first state, said at least one further battery is rechargeable, and when the system is in said second state, said first battery is rechargeable.

According to a fourth aspect, the present invention is a power management system for a power supply providing power to electrical equipment, the power supply comprising a first rechargeable battery and at least one further rechargeable battery, with each battery independently providing power to the electrical equipment through a switching means, the management system comprising a management means for controlling the operation of the switching means to place the system in a first state where the electrical equipment draws power from only the first battery or at least in a further state where the electrical equipment draws power from only said at least one further battery, and wherein the management means only allows power to be drawn from one of said first battery and said at least one further battery after said one battery has been fully charged or has a predetermined maximum level of charge.

In this aspect, the management means preferably only allows one-of said first and said at least one further batteries to be charged after that battery has reached a predetermined minimum level of charge According to a further aspect, the present invention is an implantable tissue-stimulating prosthesis that draws electrical power from a power supply that is implantable with or in the prosthesis, the power supply including a first rechargeable battery and at least one further rechargeable batten. The prosthesis can have a management system as defined herein.

In one embodiment, the tissue-stimulating prosthesis can comprise a prosthetic hearing implant. The prosthetic hearing implant can preferably operate in a stand alone mode or in concert with an externally mounted device. The externally mounted device can include a sound processor, such as a speech processor, and/or an external power supply. The prosthetic hearing implant preferably includes a sensing means that senses when the externally mounted device, incorporating an external power supply, is brought into use. On sensing of the availability of the external power supply by the sensing means, the prosthetic hearing implant preferably draws all of its electrical power requirement from the external supply. The sensing means can preferably detect removal of the external power supply and provide a suitable output to the prosthetic hearing implant that instructs it to draw power from the internal implanted power supply, if power is available.

In a further embodiment, the tissue-stimulating prosthesis can comprise a totally implantable prosthetic hearing implant system such as is described in International Application No. PCT/AU01/00769, the contents of which are incorporated by way of reference. For the purposes of the description provided below, reference will be made to the prosthesis in the form of a prosthetic hearing implant. It is to be appreciated that the following description could apply, with appropriate modification, to other systems adapted for implantation in the body.

The totally implantable prosthetic hearing implant system described in International Application No. PCT/AU01/00769 is preferably adapted to be implanted in the mastoid bone adjacent the ear of the implantee that is to receive the implant. The system includes a microphone that detects external sounds and outputs acoustic signals representative of detected sounds, a processor means that receives the acoustic signals and converts the signals, particularly signals representative of speech, into stimulation signals representative of the detected sounds and an electrode array suitable for insertion in the cochlea of an implantee that receives the stimulation signals and transmits electrical stimulations to the implantee's auditory nerves. The electrode array can be any type known in the art, such as that described in U.S. Pat. No. 4,532,930.

In a preferred embodiment of the invention, the power supply includes only the first battery and one of said at least one further batteries, ie. a second rechargeable battery. Again, for the purposes of the description that follows, reference will be made to the power supply as having only two batteries. It will be appreciated that the power supply could incorporate a third rechargeable battery or even a higher number and that the description that follows is equally applicable, with appropriate modification, to such systems.

In a further embodiment, only one of the rechargeable batteries of the implanted power supply can be used to provide power to the implant at any one time. The power supply preferably includes a power supply management means that determines which battery is used to power the implant, if at all, at any particular time.

The management means is preferably adapted such that if the first battery is powering the implant, the second battery is not used to provide power to the implant. Still further, it is preferred that if the second battery is powering the implant, the management means prevents the first battery from providing power to the implant.

In yet a further embodiment, the management means further comprises a charge monitoring means that monitors the charge in the first and second batteries. When one of the batteries is being used to provide power to the implant, for example the first battery, the monitoring means can monitor the charge in this battery. When the charge of the first battery reaches a predetermined minimum level, or is fully discharged, the monitoring means can output a signal indicative that the charge has reached this minimum level. This output signal can be provided to the management means which operates a switching means that switches the power supply for the implant from the first battery to the second battery. The use of the management means can be used to ensure a continuous source of power for the implant without intervention by the implantee.

At the same time that the monitoring means is monitoring the first battery, it can also monitor the charge in the second battery. If the charge in the second battery is also monitored by the monitoring means to be below a predetermined level or fully discharged, the management means can instead of operating switching means begin shut-down of the implant.

When in use, the first or second battery preferably provides power for the microphone, processor means, electrode array and any other electrical or electronic componentry of the implant system.

When the monitoring means detects that the charge in the first battery has reached a predetermined minimum level or is approaching, full discharge, and there is no charge in the second battery, the monitoring means preferably outputs a signal that causes the management means to generate a warning indication to the implantee that the power supply of the implant needs recharging. The warning system may generate a unique stimulus signal that the implantee is trained to recognise as indicative that the power supply needs recharging. For example, the implant may output a sound that the implantee is trained to understand as being indicative that the power supply needs recharging.

In another embodiment, the management system can further comprise an interrogation means that allows the implantee to determine the measured charge levels noted by the monitoring means of the power supply.

In one embodiment, the power supply can be mounted within a case that also encloses the componentry of the electrical equipment, such as the processor means of the prosthetic hearing implant. In another embodiment, the power supply can be mounted within a separate case with electrical connection provided between the batteries and the componentry, such as the processor means. Where the power supply is mounted in a separate case, the electrical connection is preferably disconnectable to allow removal of the power supply case, or at least the batteries, from the implantee if required.

The first and said at least one further batteries can comprise Lithium-Ion cells. It will be appreciated that any suitable battery cell could be utilised in the present invention. Both the first and second batteries are also preferably surrounded by an electrically insulating material such that the batteries are electrically insulated from the case in which they are mounted.

The prosthetic hearing implant system preferably also includes a wire antenna coil that is also implanted within the implantee. The antenna coil is preferably comprised of at least two, and preferably at least 3, turns of electrically insulated platinum or gold wire tuned to parallel resonance. The electrical insulation of the antenna coil can be provided by a flexible silicone moulding and/or silicone or polyurethane tubing. The antenna coil is preferably external of the case surrounding the processor means. The antenna coil is disposed about a centrally located magnet. The magnet can comprise a rare earth permanent magnet hermetically sealed within a titanium case. The magnet within its case is preferably held in the centre of the antenna coil by the silicone moulding surrounding the antenna coil. In a preferred embodiment, the magnet is removable from the system so as to allow the implantee to undergo magnetic resonance imaging (MRI) scanning. Electrical connection between the coil and the componentry within the case can be provided by two hermetic and insulated ceramic feedthroughs or an electrical connector. The ceramic feedthroughs can be formed using the method described in U.S. Pat. No. 5,046,242, the contents of which are incorporated herein by reference. The coil can act as an RE link to allow bidirectional data transfer between the system and external componentry thereby allowing the system to function as a conventional prosthetic hearing implant system if necessary. The coil also importantly acts a power receiver to allow inductive charging of the power supply, A battery charging means that is mounted external to the body of the implantee can be used to recharge the batteries of the power supply. Where the prosthesis is a prosthetic hearing implant having an implanted antenna coil, the battery charging means also includes an antenna coil that through use of the inductive link formed by bringing the implanted coil and the external coil adjacent each other, allows the implanted power supply to be recharged.

In a further embodiment, the battery charging means can be part of an external device having functions other than that of just charging the implanted power supply. For example, the external device can also act as an external power source for the implant. Further, where the prosthesis is a prosthetic hearing implant, the external device also preferably includes an external sound processor, such as a speech processor and operates in a similar manner as a conventional device. The external sound processor can be used, for examples to provide the implantee with the option of using sound coding algorithms not supported by the internal implanted sound processor.

It is preferred that whenever the external power source is being used by the implantee, the implanted battery source will be disconnected from the electrical equipment such as the implant, by the switching means. As such, it is preferred that whenever external power is available it is utilised as the power source by the implant. To ensure this, the management means of the implanted power supply can preferably detect when an external coil has been placed adjacent the implanted coil and that external power is available to the implant.

It is also preferred that whenever the external power source is being used by the implantee, the management system will review the output of the monitoring means and, if charging is required of a particular battery, ensure that charge is provided to allow recharging of at least that battery.

The management means is preferably adapted lo only charge one of the batteries when the charge in that battery has reached a predetermined minimum level or is fully discharged. Once charging of one of the batteries has commenced, the management means is preferably adapted to prevent use of that battery until such time as it is fully charged or has at least reached a predetermined level of charge that is greater than the predetermined minimum level. Where one battery is fully discharged and the other battery is being charged but has not reached full charge, the management means will preferably prevent the implant drawing power from the implanted power supply even when the external power source is removed or deactivated.

Once charging of one of the batteries is complete, the management means will only commence charging of another battery if the charge level of said another battery is below a predetermined minimum level or is fully so discharged.

When the batteries are fully charged, the management means is preferably adapted to stop further charging of the batteries. The management means preferably, however, continues to ensure that the implant is powered by the external power source while ever it is in place.

The management means of the present invention is designed to maximise the life of the batteries within the implanted power supply. By ensuring that a battery is only charged when its level of charge has reached a predetermined minimum level (eg. fully discharged) and is not used or discharged until its level of charge has reached a predetermined maximum level (eg. fully charged), the batteries are prevented from undergoing what is commonly known as shallow charging. It is known that shallow charging can significantly reduce the cycle life of a battery from fully charged to fully discharged. By reducing or preventing shallow charging, the useable life of the batteries will be extended to the maximum potential term so extending the effective life of the implant.

BRIEF DESCRIPTION OF THE DRAWINGS

By way of example only, a preferred embodiment of the invention is now described with reference to the accompanying drawings, in which.

PREFERRED MODE OF CARRYING OUT THE INVENTION

Figure 1:
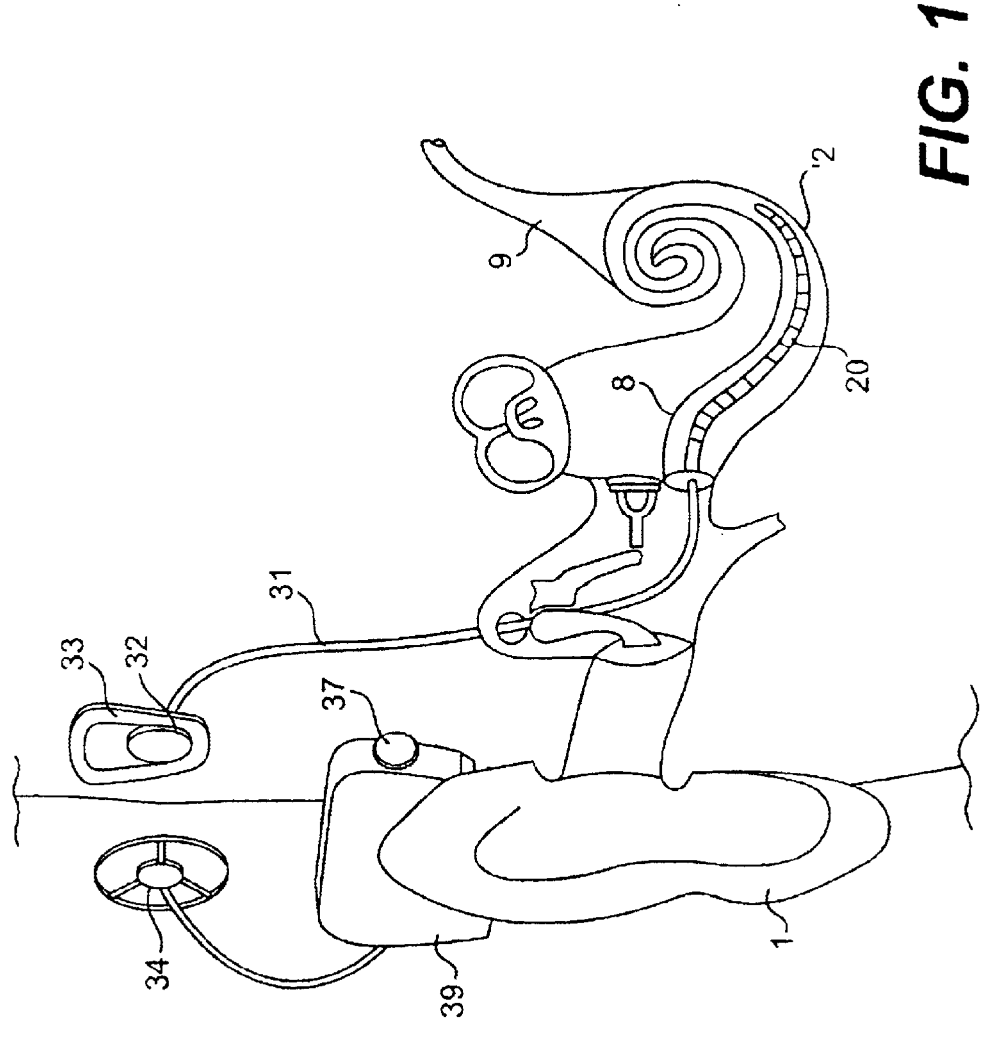
FIG. 1 is a pictorial representation of one example of a prior art prosthetic hearing implant system.

Before describing the features of the present invention, it is appropriate to briefly describe the construction of one type of known prosthetic hearing implant system with reference to FIG. 1.

Known prosthetic hearing implants typically consist of two main components, an external component including an external housing containing a speech processor 39, and an internal component including an implanted receiver and stimulator unit 32. The external component includes a microphone 37. The speech processor 39 is, in this illustration, constructed and arranged so that it can be mounted on and fit behind the pinna 1. It will be understood that in an alternative version, the housing for the speech processor 39 and/or the microphone 37 may be worn on the body. Attached to the speech processor 39 is an external antenna coil 34 which transmits electrical signals to the implanted unit 32 via a radio frequency (RF) link.

The implanted component includes a receiver antenna coil 33 for receiving power and data from the transmitter coil 34. A cable 31 extends from the implanted receiver and stimulator unit 32 to the cochlea 2 and terminates in an electrode array 20. The signals thus received are applied by the array 20 to the basilar membrane 8 thereby stimulating the auditory nerve 9. The operation of such a device is described, for example, in U.S. Pat. No. 4,532,930.

Figure 2:
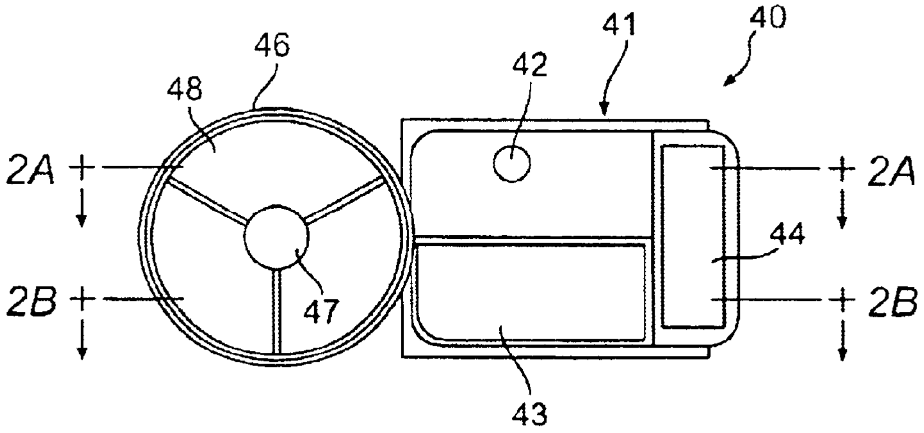
FIG. 2 is a is a plan view of an implantable housing for a prosthetic hearing implant that can use the power supply of the present invention.
Figure 2A:
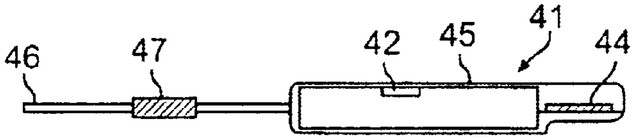
FIG. 2*a* is a cross-sectional view of the housing through line A—A of FIG. 2.
Figure 2B:
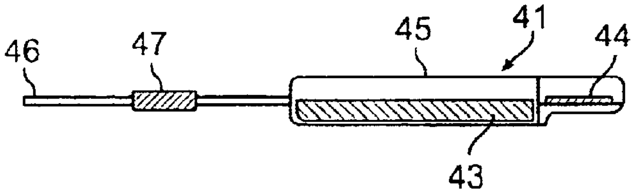
FIG. 2*b* is a further cross-sectional view of the housing of FIG. 2 through line B—B.

One example of a tissue-stimulating prosthesis of the present invention is the totally implantable prosthetic hearing implant depicted generally as 40 in FIG. 2. This implant is capable of operation, at least for a period of time as a single unit without reliance on componentry worn or carried external to the body of the implantee.

The implant 40 is adapted for implantation in the mastoid bone adjacent the ear of the implantee that is receiving the implant. The implant 40 has a similar geometry to a conventional implant unit, such as that described in U.S. Pat. No. 4,532,930. As such, surgical procedures similar to that used for conventional implants are envisaged to be used when implanting the current invention.

The implant 40 comprises a biocompatible, hermetically sealed titanium case 41 that houses the key electronic circuitry 44 of the implant 40. Also housed within the case 41 is a microphone 42 and a power supply 43. Prior to implantation, the case 41 is coated with a layer of silicone or parylene that serves to further protect the implant. Such procedures are well known in the art and will not be further discussed in this application.

As previously mentioned, the case 41 is formed so as to minimise the need for bone excavation from the mastoid bone at implantation. Whilst the actual dimensions of the case are not important to the understanding of the invention it should be appreciated that the case is designed so that the overall dimensions of the implant are substantially the same or marginally greater than those of a conventional implant. This design allows for similar surgical techniques to be employed during implantation of the current invention as well as with the conventional implant.

In this particular embodiment, the microphone 42 is mounted adjacent the surface 45 of the case that faces outwardly following implantation of the case. The depicted microphone 42 is a directional dual cavity microphone but it is envisaged that other microphones could be employed in this system which could perform an equal function. Use of such a microphone provides an effective means of rejecting common mode body-conducted noise emanating from body functions, such as chewing, respiration and blood flow. Whilst the preferred microphone 42 is an electret-type microphone, it will be appreciated that other microphone types could be utilised by the present invention.

The electrode array used in the present invention can be identical to the array 20 known from the prior art. It is, however, preferred that the implant 40 use a Contour array as developed by Cochlear Limited in conjunction with corticosteroids to reduce the current required for stimulation.

The implant 40 includes an antenna coil 46, which is attached externally of the casing 41. The depicted coil is a 3-turn electrically insulated platinum wire antenna coil. The electrical insulation for the antenna coil 46 is provided by a flexible silicone moulding. The antenna coil extends externally from the case 41 as can be seen in FIG. 1.

The antenna coil 46 is preferably disposed about a centrally located rare earth permanent magnet 47 that is held in the centre of the antenna coil 46 by the silicone moulding 48 surrounding the antenna coil 46. The provision of the magnet assists in the alignment of an external coil unit with the implanted coil 46 via magnetic attractive forces, thereby providing for the system to be used as a conventional prosthetic hearing implant system when and if required. The magnet 47 is preferably surgically removable so as to allow the implantee to undergo, if required, magnetic resonance imaging (MRI) scanning.

Electrical connection between the coil 46 and the componentry within the case 41 is provided by two hermetic and insulated ceramic feedthroughs. The coil 46 can act as an RF link to allow bidirectional data transfer between the implant 40 and external devices (described below). The coil 46 also acts as a power receiver and also provides a means of inductively charging the power supply 43 through the RF link.

The circuitry 44 within the case is preferably mounted on a flexible circuit board to allow for easier provision of the circuitry within the case 41. The circuitry 44 in the depicted embodiment includes a sound processor and a stimulation processor incorporated within a single integrated circuit.

The power supply 43 provides power for the microphone 42 and the electronic circuitry 44 housed within the case 41.

In the depicted embodiment, the power supply 43 incorporates two Lithium-ion cells. A greater number of cells could be incorporated in the power supply 43 if space constraints allowed their inclusion. It will be appreciated by persons skilled in the art that the type of cell chosen will depend greatly on the system requirements.

In the depicted embodiment, the power supply 43 is non-removable from the case 41. It will be appreciated that in other embodiments, the case could be modified to allow removal of the power supply by surgically accessing the case 41. In order to isolate the power supply 43 from the entire package, a thermal and electrical insulating material is provided between the supply 43 and the surrounding case 41.

The implant 40 has a management system that is designed to manage the power output by the power supply 43 to the implant 40 without the need for implantee intervention. The management system is set up to ensure that the cells are fully charged before use, and when they are used are not recharged until they have been fully discharged. The goal of the management system is to maximise cell life. In the depicted embodiment the power supply management system incorporating a management means and switching means is incorporated in the electronic circuitry 44.

The electrical architecture of the circuitry 44 is based an a microcontroller adapted to perform the main control functions of the implant 40. The microcontroller provides overall supervision, configuration and control of the implant 40 and also performs the function of the stimulation processor. The stimulation processor performs the stimulation strategy process, stimulus level mapping and output control. The input to the stimulation processor comes from either an internal signal processor in the implant 40 or an external sound processor, such as speech processor 39 depicted in FIG. 1. The output from the microcontroller provides the direction to stimulate the electrodes of the array.

The totally implantable prosthetic hearing implant 40 can be used in conjunction with one or more external devices. One external device can be an external sound processor that is powered by an external battery and receives acoustic signals from an external microphone, such as microphone 37 depicted in FIG. 1. The output of the external speech processor is fed through the RF link provided in part by implanted coil 46 to the microcontroller. The external speech processor night be used when the implanted processor is inactive for any reason, such as due to flat batteries or due to a malfunction. The external processor also provides the implantee with the option of using sound coding algorithms not supported by the internal speech processor.

A further external device that can be used with implant 40 is a battery charger. The charger provides a means of inductively recharging the two batteries through the RF link provided in part by coil 46.

Figure 3:
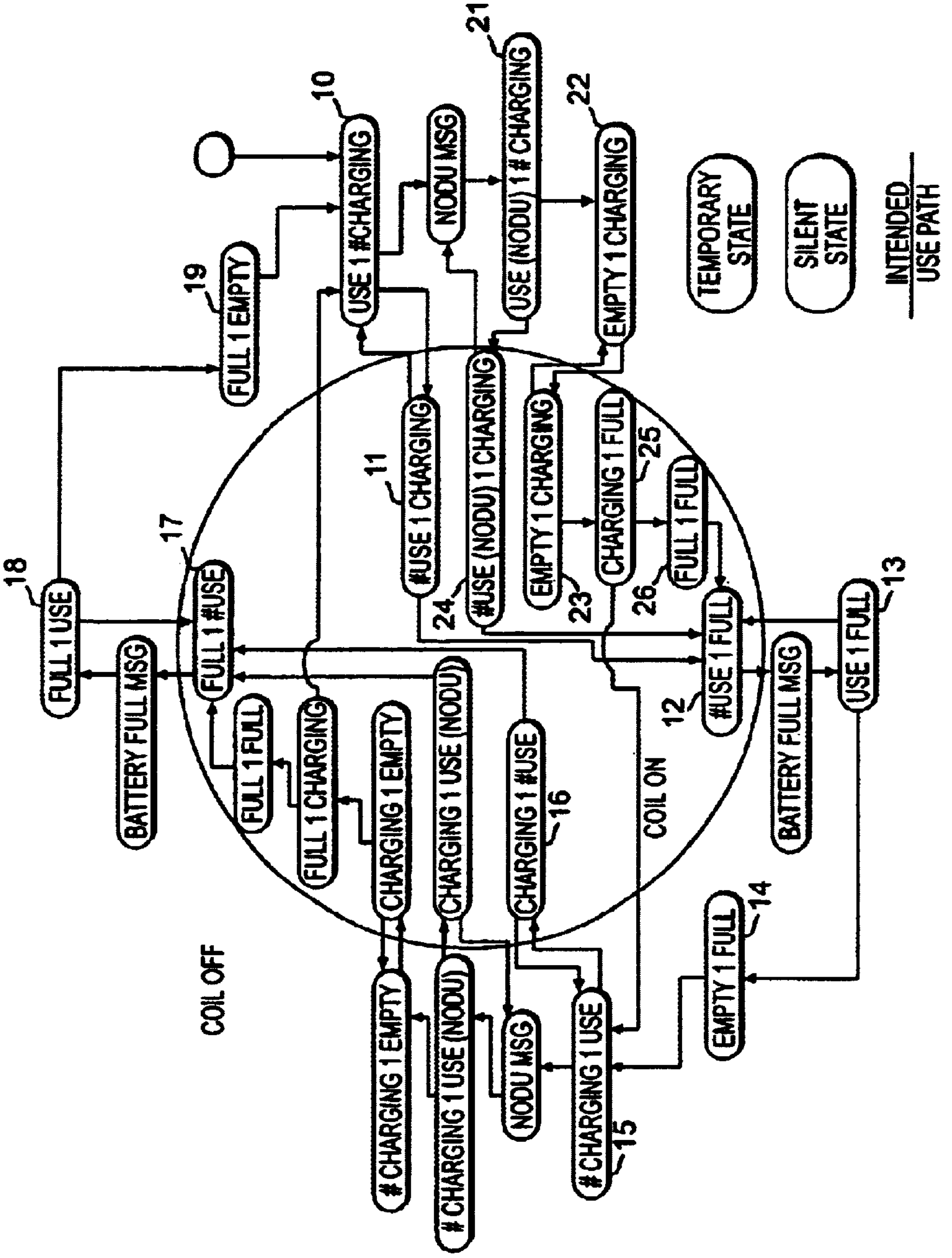
FIG. 3 is a flowchart depicting the possible operating states of the battery management system of the power supply for the implant.

FIG. 3 is a flowchart depicting the states the management system of the power supply 43 passes through while the system is in the "PROVIDE HEARING" state. The flowchart is from the implantee's perspective. The management system could be constructed incorporating a processor means and a switch device that constitutes part of or is under the control of the microcontroller. The processor means runs a loaded software program that allows it to control the status of the power supply 43 and the operation of the switch device to ensure that the implant 40 can draw power from the appropriate cell of the power supply when appropriate. There are clearly other means by which such a function could be performed; such means may include dedicated analogue and digital electronic circuitry. The described means is merely an example of one particular method of operation.

The flowchart demonstrates that the goal of the management system is to avoid shallow charging of either battery cell and to ensure that through correct usage of the device the internal power supply will always have sufficient power to ensure that the device can operate as a stand-alone device if absolutely required. The flowchart also demonstrates that the management system is set up to ensure that the implant 40 will use external power for its operation, at least for its sound processing, whenever it is available. Moreover, whenever the system is in the "COIL ON" state then that condition will be met. By "COIL ON", it is to be understood that an external coil connected to an external sound processor and power supply, as are known in the art, are being worn by the implantee.

As described, the depicted power supply 43 uses two cells. At any time, under normal operation, one cell is assigned to charging, and one to discharging. When one cell becomes discharged, and the other is fully charged the roles are reversed. This path may be seen easily by following the bold line, which is the intended use path of the power supply 43.

A basic principle of the management system is that a cell must be fully charged before it can be discharged, and it must be fully discharged before it can be charged.

The flowchart is symmetric between the cells. The cells of the power supply 43 are identified by their numbers "0" and "1". Each state thus may have a "mirror" state where the cell numbers are interchanged. Out of each pair of mirror states, only one is described in the following text for the purposes of clarity.

Each cell can be in one of four (major) states, namely "FULL", "USE", "EMPTY"and "CHARGING". A cell will cycle between these states in this order.

The management system has two clear rules governing the state: transitions of the cells:

1) cells cannot be charged when external power is not available (ie. when the external coil is not being worn or "COIL OFF").

2) cells should not be used, ie. discharged, when external power is available (ie. when the external coil is being worn or "COIL ON").

The flowchart has an entry point but no exit point—as the power supply is adapted to operate in an endless cycle.

In the flowchart, the symbol "#" is used to indicate that a cell is in a given state (eg charging) but that that function is suspended for some reason (eg the external coil is not being worn). A cell state can thus be written in the form:

"0 {Optional negation} (State) 1 {Optional negation} (State)"

where (State) can be one of "FULL", "USE", "EMPTY" and "CHARGING".

For example, "0 USE 1 #CHARGING" indicates that cell 0 is being used, and 1 is available for charging but that this is not possible for some reason (presumably because the external coil is not being worn).

For the purposes of following the flowchart, it is assumed that initially cell 0 is fully charged and in USE (ie. the switch device is set such that the implant 40 is drawing power from cell 0) while cell 1 is EMPTY and is capable of being charged but is not being charged because the external coil is not being worn. This condition is represented by state 10 "0 USE 1 #CHARGING".

The power supply 43 remains in state 10 until one of two actions occur. The first is where the implantee has used the implant 40 to the point where 0 cell has less than one days use left (represented by the acronym "NODU" for "Not one day's use left"). In this case, the management system issues a warning indication (ie. "NODU Msg) to the implantee (such as an audible tone) and moves into state 21 "0 USE (NODU) 1 #CHARGING" which is discussed below.

The second action that can be taken is that the implantee attaches the external coil and commences use of the external power supply for the implant 40. In this case, the management system operates the switch device and disconnects cell 0 of the power supply and allows cell 1 to be charged whilst the external power supply also provides the power to operate the device in the same way as a conventional implant, so moving the power supply into state 11 "0#USE 1 CHARGING", ie. cell 1 is being charged and cell 0 is available for use but this is blocked as external power is available.

If the external coil is then removed, the management means again operates the switch device and the power supply reverts to state 10 as indicated in the flowchart. If cell 1 becomes fully charged, the power supply moves to state 12 "0 #USE 1 FULL". This describes a state where the implantee has attached the coil, cell 0 is available for use, but this is blocked because external power is available, and cell 1 is fully charged and so is not charged even though power is available through the external coil.

State 12 is left if the external coil is removed and the power supply moves to state 13 "0 USE 1 FULL" (ie. a state where cell 0 is being used, and cell 1 is full). In moving from state 12 to state 13, the management system operates the switch device to allow the implant 40 to draw power from cell 0. The management system also outputs an indication (eg. "Battery full msg" ) indicating to the implantee that the cell is full. A suitable message might be in the form of a short sound, such as a beep.

Once in state 13, the power supply 43 can provide power to the implant 40 for a period dependent on the amount of charge in cell 0. This could last for several days.

The power supply 43 can revert to state 12 if the external coil is again worn by the implantee. Otherwise, state 13 is left when the "in use" cell 0 is discharged as indicated by state 14 "0 EMPTY 1 FULL", State 14 is a transitional state as 0 cell is not available for use as it is empty, and if cell 1 is used at all it immediately ceases to be full. At this point in the flowchart, the roles of the cells within the system are swapped.

State 14 is left upon the assignment by the management system of cell 1 for use, and cell 0 for charging and the power supply so moves to state 15 "0 #CHARGING 1 USE". In this state, cell 0 is not charged as the external coil is not being worn. It will be appreciated that state 15 is the mirror of state 10 "0 USE 1 #CHARGING". If the external coil is again worn by the implantee, the power supply moves to state 16 "0 CHARGING 1 #USE". The power supply 43 reverts to state 15 if the external coil is removed before 0 cell is fully charged. Once 0 cell is fully charged, the power supply shifts to state 17 "0 FULL 1 #USE" where the implant 40 is powered by the external power supply and no charging of either cell occurs.

If the external coil is removed after the power supply 43 has moved to state 17, the power supply shifts to state 18 "0 FULL 1 USE". When initially shifting to state 18, the power supply outputs an indication (eg. "Battery full msg") indicating to the implantee that the cell is full. A suitable message again might be in the form of a short sound, such as a beep.

If the external coil is reattached, the power supply shifts back to state 17 where the external coil is used to power the implant 40 and no charging occurs. Once in state 18, the power supply 43 can provide power to the implant 40 for a period dependent on the amount of charge remaining in cell 1. This could last for several days.

State 18 is left when the "in use" cell (cell 1) is discharged as indicated by state 19 "0 FULL 1 EMPTY". State 19, like state 14, is a transitional state as cell 1 is not available for use as it is empty, and if cell 0 is used at all it immediately ceases to be full. Accordingly, at this point, the power supply has returned to state 10 ready to repeat the cycle as required.

The cycle described above is the normal power cycle for the power supply. This describes the status path taken by the power supply 43 day-to-day. It is designed for implantees who want to keep their cell charged using a daily cycle, that they can fit into their lifestyle. For example, charging could occur while driving the car to work and back. In summary, the implantee is required to wear an external speech processor (or external battery charger) for a certain number of hours per day (on average), and the management system ensures that the appropriate cell is charged when appropriate. Such a system has significant advantages over an implant having a single cell as the implantee has to schedule times to charge the cell. These times have to fit with the times when the cell is flat rather than being at the convenience of the implantee, if the implantee is to avoid shallow charging the cell in their implant. Therefore, if the implantee sets aside a specified time period each day to wear an external unit (with the implant functioning as a traditional implant during this time) then the charging function is managed automatically by the implant itself without the need for implantee input.

As was briefly described above, the power supply 43 can enter an abnormal power cycle if insufficient power is provided to the implant 40 to allow it to use its normal power cycle. As described above, if the implantee uses the implant 40 with the external coil detached (eg State 10 "0 USE 1 #CHARGING") then the 0 cell will eventually discharge until the point is reached where it no longer has enough power to sustain one day's use. The implant then sends the "not one day's use" (NODU) message to the implantee. This is done by generating a "beep" with an easily recognisable characteristic or possibly a simulated voice warning of this condition. Such a message is also generated if the implantee disconnects the external coil (ie. speech processor or cell charger) before cell 1 is fully charged and is available for use when the external coil is removed.

Once the NODU message has been generated, the power supply moves to state 21 "0 USE (NODU) 1 #CHARGING". In this state, the implant 40 is operational but the cell has less than one day's use available, so will shut down after some time.

State 21 is left by one of two paths. Firstly, state 21 can be left when 0 cell no longer has sufficient charge to sustain power to the implant 40. In this case, the power supply moves to state 22 "0 EMPTY 1 #CHARGING". State 22 is a "silent state" where the implant 40 is non-operational. It will be appreciated that while in state 22, 0 cell is regarded as empty, the power supply 43 may have sufficient power to power certain processor functions, such as maintain any loaded programs.

The power supply can move from state 22 to state 23 "0 EMPTY 1 CHARGING" when an external coil is attached so that charging can begin. State 22 may be re-entered if the coil is detached before the cell 1 is fully charged and is available for use.

State 21 can also be left if the implantee on hearing the NODU message decides to charge the cell by wearing the external coil (ie. speech processor or battery charger). In this case, the power supply moves to state 24 instead "0 #USE (NODU) 1 CHARGING". While in state 24, the "in use" cell still has less than one day's use, so this state is distinct from other charging states.

State 24 is left when cell 1 is full and so can be assigned for use. In this case, the power supply moves back to state 12 and is back in the normal power cycle.

If the power supply is in state 23 "0 EMPTY 1 CHARGING", the power supply will remain in this state while the external coil is attached until 1 cell is full, ie state 25 "0 CHARGING 1 FULL". If the external coil remains attached for a sufficient period of time, the power supply moves into state 26 "0 FULL 1 FULL". Once in this state, the management system can switch 0 cell to not in use and so the power supply reverts to state 12 in the normal power cycle.

If the external coil is removed while the power supply is in state 25, The power supply shifts to state 15 with the power supply using cell 1 to provide power to the implant 40, Careful inspection of the flowchart reveals that if the implantee ignores either instance where the NODU message is generated, then one cell receives one more charge/discharge cycle than the other. This will result in asymmetric use of the cells. While undesirable, it is envisaged that over the life of the power supply (eg. 1000 or more charge/discharge cycles) this should balance out. It will be appreciated that ideally the two cells should be used symmetrically, so they wear out at the same rate. Asymmetric use of the cells could be avoided by exiting state 26 "0 FULL 1 FULL" and entering state 17 "0 FULL 1 #USE" (the mirror state of state 12).

It will be appreciated from a review of the flowchart that the management system for the power supply ensures that hearing is provided both when the external device is attached or detached (so long as at least one cell is charged). This allows the implantee to interrupt charging if it is not convenient without the danger of causing shallow charging of the power supply.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A medical implant, comprising:

a prosthetic hearing implant having a power management system, a power supply comprising:

a first rechargeable battery, and at least one further rechargeable battery;

a switching means, wherein each battery independently provides power to said hearing implant through said switching means; and a management means for controlling said switching means, wherein said switching means has the capability to place said power management system in a first state where said prosthetic hearing implant draws power from only said first battery and has the capability to place said power management system in at least a further state where said prosthetic hearing implant draws power from only said at least one further battery, and wherein the power supply provides power to the prosthetic hearing implant.

2. An implantable tissue-stimulating prosthesis comprising a power supply comprising:

a first rechargeable battery, and at least one further rechargeable battery;

a switching means, wherein each battery independently provides power to said prosthesis through said switching means; and a power management system for said power supply, wherein said management system comprises a management means for controlling the operation of said switching means, wherein said switching means places said power management system in a first state where said prosthesis draws power from only said first battery and wherein said switching means places said power management system in at least a further state where said prosthesis draws power from only said at least one further battery, wherein said prosthesis draws power from said power supply, and wherein said power supply is implantable with or in said prosthesis.

3. An implantable tissue-stimulating prosthesis of claim 2 wherein said prosthesis is a prosthetic hearing implant.

4. An implantable tissue-stimulating prosthesis of claim 3 wherein said prosthetic hearing implant is implantable and comprises a microphone for detecting external sounds and outputting acoustic signals representative of detected sounds, a processor means for receiving said acoustic signals and converting said acoustic signals into stimulation signals representative of said detected sounds and an electrode array suitable for insertion in the cochlea of an implantee that receives said stimulation signals and transmits electrical stimulations to the implantee's auditory nerves.

5. An implantable tissue-stimulating prosthesis of claim 4 wherein said management means further comprises a charge monitoring means for monitoring the charge in said first battery and said at least one further battery.

6. An implantable tissue-stimulating prosthesis of claim 5 wherein when the charge of said first battery is monitored by said monitoring means to have reached predetermined minimum level, or is fully discharged, said monitoring means outputing a signal indicative that the charge has reached said predetermined minimum level.

7. An implantable tissue-stimulating prosthesis of claim 6 wherein said output signal is provided to said management means to operate said switching means to switch said power supply for said implant from said first battery to said at least one further battery.

8. An implantable tissue-stimulating prosthesis of claim 7 wherein at the same time that said monitoring means is monitoring said first battery, said monitoring means can also monitor the charge in said at least one further battery.

9. An implantable tissue-stimulating prosthesis of claim 8 wherein when said monitoring means detects that the charge in said first battery has reached a predetermined minimum level, and there is no charge in said at least one further battery, said monitoring means outputting a signal to said management means whereby said management means generates a warning indication to the implantee that said power supply of the implant needs recharging.

10. An implantable tissue-stimulating prosthesis of claim 9 wherein said warning indication is a unique stimulus signal to indicate that said power supply needs recharging.

11. An implantable tissue-stimulating prosthesis of claim 9 wherein said management system further comprises an interrogation means for allowing the implantee to determine the measured charge levels noted by said monitoring means.

12. An implantable tissue-stimulating prosthesis of claim 4 wherein said first battery and said at least one further battery comprise Lithium-Ion cells.

13. An implantable tissue-stimulating prosthesis of claim 4 wherein said prosthetic hearing implant further comprises a wire antenna coil that is implantable within the implantee.

14. An implantable tissue-stimulating prosthesis of claim 13 wherein a battery charging means is mountable external to the body of the implantee and adapted to recharge said first battery and said at least one further battery of said power supply.

15. An implantable tissue-stimulating prosthesis of claim 14 further comprising an external device, wherein said external device comprises:

said battery charging means; and at least an external speech processor.

16. An implantable tissue-stimulating prosthesis of claim 3 wherein said implant further comprises an external device, wherein said external device is mountable external to the implantee.

17. An implantable tissue-stimulant prosthesis of claim 16 wherein said external device comprises a speech processor and an external power supply.

18. An implantable tissue-stimulating prosthesis of claim 17 wherein said management means further comprises a sensing means for sensing when said external power supply is brought into use.

19. An implantable tissue-stimulating prosthesis of claim 18 wherein upon sensing of the availability of said external power supply by said sensing means, said hearing implant draws all of said prosthetic hearing implant's electrical power requirement from said external supply.

20. An implantable tissue-stimulating prosthesis of claim 18 wherein said sensing means detects removal of said external power supply and provides a suitable output to said hearing implant that instructs said prosthetic hearing implant to draw power from said power supply, if power is available.

* * * * *